US012654015B2

(12) United States Patent
Meyers et al.

(10) Patent No.: US 12,654,015 B2
(45) Date of Patent: Jun. 16, 2026

(54) DISTRIBUTED DEVICE CONTROL AND WEARABLE SYSTEM FOR VAGUS NERVE STIMULATION

(71) Applicant: Battelle Memorial Institute, Columbus, OH (US)

(72) Inventors: Eric Meyers, Columbus, OH (US); Patrick Ganzer, Columbus, OH (US); Seyed Masoud Loeian, Columbus, OH (US); Ian Baumgart, Columbus, OH (US); Joshua Branch, Westerville, OH (US)

(73) Assignee: Battelle Memorial Institute, Columbus, OH (US)

( * ) Notice: Subject to any disclaimer, the term of this patent is extended or adjusted under 35 U.S.C. 154(b) by 792 days.

(21) Appl. No.: 17/738,544

(22) Filed: May 6, 2022

(65) Prior Publication Data

US 2022/0355113 A1 Nov. 10, 2022

Related U.S. Application Data

(60) Provisional application No. 63/185,472, filed on May 7, 2021.

(51) Int. Cl.
*A61N 1/36* (2006.01)

(52) U.S. Cl.
CPC ...... *A61N 1/36139* (2013.01); *A61N 1/36114* (2013.01)

(58) Field of Classification Search
CPC ............ A61N 1/36139; A61N 1/36114; A61N 1/0456; A61B 5/4836; A61B 5/00;
(Continued)

(56) References Cited

U.S. PATENT DOCUMENTS

| | | |
|---|---|---|
| 7,167,751 B1 | 1/2007 | Whitehurst et al. |
| 10,953,229 B1 | 3/2021 | Ganzer et al. |

(Continued)

FOREIGN PATENT DOCUMENTS

| | | |
|---|---|---|
| AU | 2017315764 B2 | 2/2019 |

OTHER PUBLICATIONS

Search Report and Written Opinion for International Application No. PCT/US22/28109 dated Sep. 28, 2022.
(Continued)

*Primary Examiner* — Mark W. Bockelman
(74) *Attorney, Agent, or Firm* — McDonald Hopkins LLC

(57) ABSTRACT

A stimulation system may include a sensor configured to detect a physiological signal of a user, the physiological signal having a biomarker therein associated with a disorder of the user; a stimulator configured to deliver electrical stimulation to the user; and a hub device configured to receive the physiological signal from the sensor and to output a control signal to the stimulator. The control signal may cause the stimulator to deliver electrical stimulation to the user according to a stimulation protocol, the stimulation protocol treating the disorder. The hub device may be configured to output the control signal based on the biomarker of the received physiological signal. The hub device may be configured to generate another control signal for treating another disorder based on a biomarker not included in the physiological signal received from the sensor.

19 Claims, 3 Drawing Sheets

(58) Field of Classification Search
    CPC ........ A61B 5/021; A61B 5/318; G16H 20/30;
                    G16H 40/67; G16H 50/20
    See application file for complete search history.

(56)                    References Cited

U.S. PATENT DOCUMENTS

| 2004/0186517 | A1 | 9/2004 | Hill et al. |
| 2010/0114211 | A1 | 5/2010 | Donofrio et al. |
| 2011/0301658 | A1 | 12/2011 | Yoo et al. |
| 2016/0375251 | A1 | 12/2016 | Bonnet et al. |
| 2019/0274655 | A1 | 9/2019 | Thakur et al. |
| 2021/0085979 | A1 | 3/2021 | Ganzer et al. |

OTHER PUBLICATIONS

Extended Search Report for European Application No. 22799695.6
dated Sep. 13, 2024.

DISTRIBUTED DEVICE CONTROL AND WEARABLE SYSTEM FOR VAGUS NERVE STIMULATION

BACKGROUND

Vagus nerve stimulation (VNS) is as a neuromodulation therapy for the treatment of epilepsy, depression, stroke, and other disorders. Unfortunately, there are currently no reliable biomarkers that can monitor VNS efficacy and the downstream effects of stimulation, and that can be measured longitudinally and non-invasively. Conventional vital signs, such as heart rate and blood pressure, fail to robustly measure stimulation efficacy due to the complex interplay of the sympathetic and parasympathetic nervous systems on these metrics. Thus, current techniques to effectively monitor modulation of the central nervous system involve expensive imaging or blood biomarker analyses. As a result, problems that prevent a VNS stimulator from effectively activating the Vagus nerve can go undetected for weeks or months.

Furthermore, determining when to apply stimulation often requires clinical intervention—that is, a clinician monitoring a patient and manually delivering the stimulation therapy. For example, VNS may be used to treat cardiovascular disease, which is the leading cause of mortality worldwide. Although several devices and sensors now exist to monitor cardiovascular state and overall user function, cardiovascular data can be complex. Unfortunately, there is no clear way to combine this information together and analyze it to determine when and how to deliver stimulation and/or to enhance monitoring capability.

Similarly, VNS may be delivered as part of a therapy for stress disorders, such as post-traumatic stress disorder (PTSD), which can occur after experiencing a trauma and severely impact a person's wellbeing. About 8% of the population will have PTSD at some point in their lives, and 8 million adults have PTSD during a given year in the United States. Vagus nerve stimulation (VNS) has emerged as a strategy to promote neural plasticity, enhance memory, and reduce conditioned fear when delivered coincidentally with cue presentation during exposure therapy (i.e., 'overwrite' the fear memory). In addition to VNS enhancing memory consolidation and fear extinction, VNS also has an immediate anxiolytic effect that can bring immediate stress relief to the user. Thus, current therapies involve repeatedly exposing a patient, such as a patient with stress disorders, for trigger and then delivering VNS to suppress previously learned associations through the formation of new associations during the therapy-exposed triggers. However, delivering VNS to a user during exposure therapy also requires a therapist to interact with the user and identify when the user has a heightened stress response. The therapist must then manually deliver the VNS. Due to this and other complications, these therapies show high incidence of non-response, dropout, and relapse (>50%).

Additionally, electrical stimulation parameters are typically chosen by increasing the stimulation amplitude to just below the maximum tolerable level. Although more effective stimulation parameters may exist, current clinical practice is unable to effectively test and identify those parameter sets.

BRIEF SUMMARY

According to one example, the present disclosure relates to a stimulation hub system. The system may include a sensor configured to detect a physiological signal of a user, the physiological signal having a biomarker therein associated with a disorder of the user. The system may include a stimulator configured to deliver electrical stimulation to the user. The system may include a hub device configured to receive the physiological signal from the sensor and to output a control signal to the stimulator. The control signal may cause the stimulator to deliver the electrical stimulation to the user according to a stimulation protocol, the stimulation protocol treating the disorder. The hub device may be configured to output the control signal based on the biomarker of the received physiological signal. The hub device may be configured to generate another control signal for treating another disorder based on a biomarker not included in the physiological signal received from the sensor.

In various embodiments of the above example, the system may further comprise a database configured to store detected physiological signals and/or associated stimulation protocols from a plurality of users, the physiological signals being transmitted to the database by a hub device associated with each of the plurality of users; the disorder is a cardiovascular disorder and the biomarker is a pre-ejection period; the hub device is in communication with another device associated with a clinician and is configured to transmit information indicating a physiological state of the user and/or the delivery of electrical stimulation to the another device associated with the clinician; the electrical stimulation is delivered to the Vagus nerve of the user; the sensor and/or the stimulator are external to and distinct from the hub device, and the hub device is portable; and/or the hub device is configured to change the control signal to the stimulator based on the physiological signal received from the sensor.

According to another example, the present disclosure relates to a stimulation system. The system may include a sensor configured to detect a physiological signal of a user, the physiological signal having a biomarker therein associated with a disorder of the user. The system may include a stimulator configured to deliver electrical stimulation to the user. The system may include a hub device configured to receive the physiological signal from the sensor and to output a control signal to the stimulator. The control signal may cause the stimulator to deliver the electrical stimulation to the user according to a stimulation protocol, the stimulation protocol treating the disorder. The hub device may be configured to output the control signal based on the biomarker of the received physiological signal. The sensor and/or the stimulator may be external to and distinct from the hub device, and the hub device is portable.

In various embodiments of the above example, the system may further comprise a trained machine learning system remote from, and in communication with, the hub device, wherein the trained machine learning system is configured to: determine whether to deliver the electrical stimulation, and/or to determine the stimulation protocol, based on the physiological signal; and transmit the determination to the hub device, wherein the hub device is further configured to transmit the physiological signal of the user to the trained machine learning system, and wherein the control signal is based on the determination transmitted by the trained machine learning system; the system may further comprise a remote database configured to store detected physiological signals and/or associated stimulation protocols from a plurality of users, the physiological signals being transmitted to the remote database by a hub device associated with each of the plurality of users, wherein the trained machine learning system is repeatedly retrained based on the detected physiological signals and/or associated stimulation protocols stored in the remote database; the trained machine learning system is configured to: extract one or more biomarkers of the physiological signal of the user that are indicative of one or more disorders; predict an outcome of the stimulation protocol based on an analysis of the one or more biomarkers; and determine, based on the prediction, whether to deliver the electrical stimulation the user according to the stimulation protocol; the hub device is in communication with another device associated with a clinician and is configured to transmit information indicating a physiological state of the user and/or the delivery of electrical stimulation to the another device associated with the clinician; and/or the electrical stimulation is delivered to the Vagus nerve of the user.

According to still another example, the present disclosure relates to a stimulation method. The method may include identifying a disorder for treatment. The method may include determining a biomarker indicative of the disorder. The method may include determining a treatment stimulation protocol. The method may include selecting a sensor configured to detect the biomarker. The method may include selecting a stimulator configured to apply the treatment stimulation protocol. The method may include configuring a hub device external to and distinct from the sensor and the stimulator to apply the treatment stimulation protocol based on the biomarker detected by the sensor, the sensor and the stimulator being connected to the hub device; then: the method may include identifying a second disorder for treatment. The method may include determining a second biomarker indicative of the second disorder. The method may include determining a second treatment stimulation protocol. The method may include selecting a second sensor configured to detect the second biomarker. The method may include selecting a second stimulator configured to apply the second treatment stimulation protocol. The method may include reconfiguring the hub device to apply the second treatment stimulation protocol based on the second biomarker detected by the second sensor.

In various embodiments of the above example, the disorder is a cardiovascular disorder and the biomarker is a pre-ejection period; the hub device is in communication with another device associated with a clinician and is configured to transmit information indicating a physiological state of the user and/or the delivery of electrical stimulation to the another device associated with the clinician; the electrical stimulation is delivered to the Vagus nerve of the user; the hub device is portable; and/or the hub device is configured to change a control signal to the stimulator based on the physiological signal received from the sensor.

DETAILED DESCRIPTION

Considering the above, the present disclosure relates at least to improved treatments of neurological and psychological disorders, (e.g., anxiety disorders including stress disorders, PTSD, obsessive compulsive disorder (OCD), panic disorders, social phobias, and the like), cardiovascular conditions, and addiction disorders, by using electrical stimulation such as Vagus nerve stimulation (VNS). The present disclosure also relates to improved monitoring and control of the efficacy and the downstream effects of the stimulation. Such systems and methods may include a wearable system that measures physiological parameters (including advanced cardiovascular physiology, beyond conventional heart rate and blood pressure metrics) to control stimulation, to continuously monitor stimulation efficacy, and/or to provide feedback to both the user and clinician.

Figure 1:
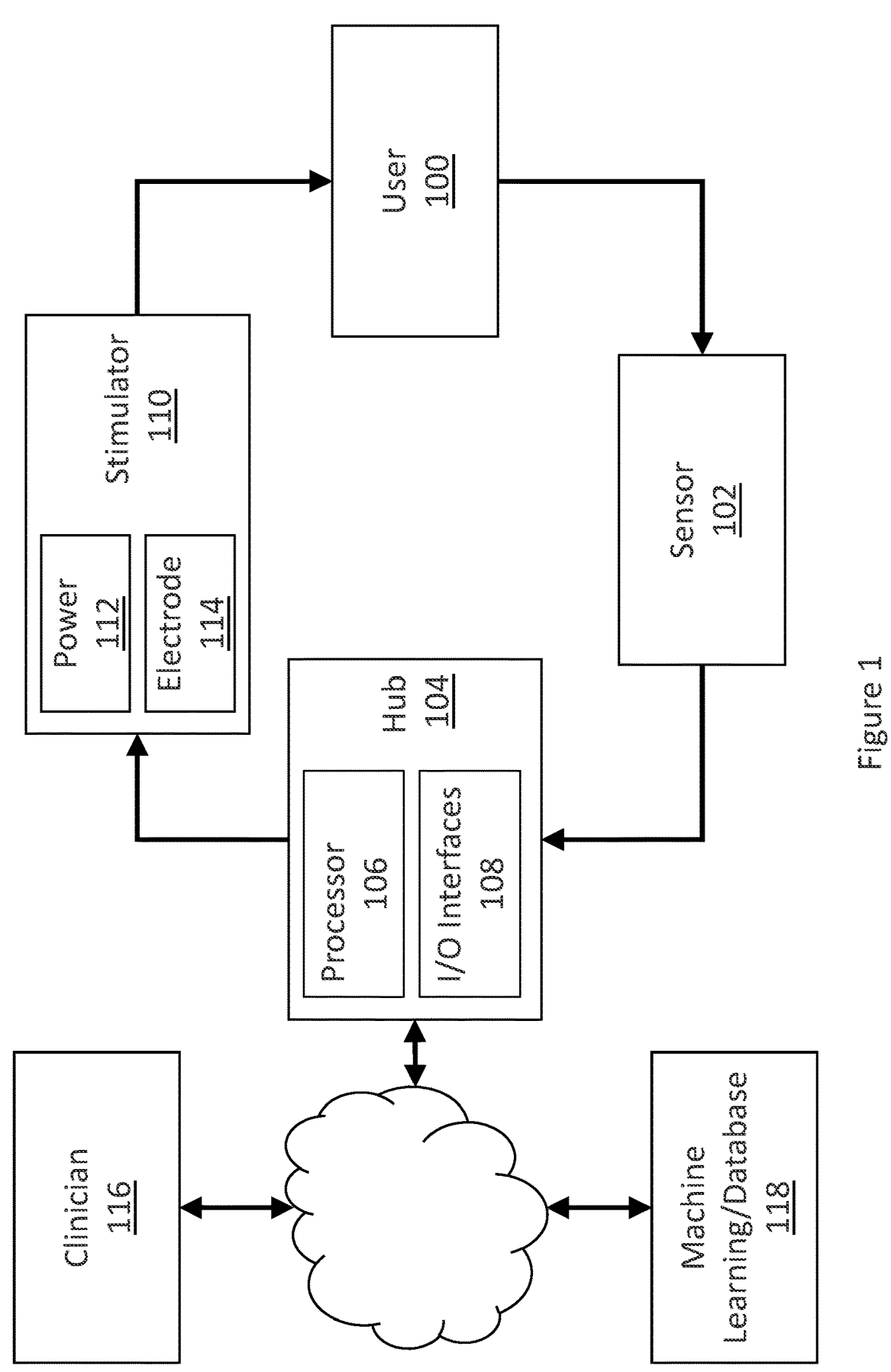
FIG. 1 illustrates an example stimulation hub system according to the present disclosure.

FIG. 1 illustrates a stimulation hub system of the present disclosure. Although FIG. 1 illustrates single instances of the components of the stimulation hub system, the system of FIG. 1 may include any number of each component. Therein, at least one sensor 102 monitors physiological data from a user 100. The data collected by the sensor(s) 102 is input to a hub device 104, which includes, for example, at least one processor 106 and input/output (I/O) interfaces 108 through which the sensor(s) 102 may be connected (wired or wirelessly). The hub device 104 may be wearable or otherwise portable, and thus usable outside of clinical settings. For example, the hub device 104 may be wearable in a pocket, as attached to a backpack, attached to a belt, attached to a wheelchair, or the like. The processor 106 and/or a remote machine learning system 118 are configured to process and analyze the data from the sensor(s) 102 to determine whether electrical stimulation of the user 100 is appropriate and/or to analyze the efficacy of the stimulation to make adjustment to the stimulation parameters. In some embodiments, the processor 106 may implement a trained machine learning system locally for analyzing the data from sensor(s) 102, and/or be programmed based on triggers identified by a trained machine learning system. In other words, processing of information from sensor(s) 102 may be performed locally and/or remotely. In some embodiments, the features of machine learning system and/or database 118 may be embodied by processor 106 of the hub device 104. Adjustable stimulation parameters include amplitude, frequency, pulse width, duration, and/or the like. The parameters may be adjusted, for example, if the user begins to desensitize to stimulation.

When stimulation, or modification of stimulation, is determined to be appropriate, the hub device 104 is configured to output a control signal to a stimulator 110 via I/O interfaces 108. As with the sensor(s) 102, the stimulator 110 may be connected wired or wirelessly. The control signal then causes the stimulator 110 to deliver the stimulation (e.g., VNS) to the user 100 according to a stimulation protocol. The stimulator may include a power source 112 that provides a stimulation voltage or current according to stimulation parameters to an electrode 114, which then applies the stimulation to the user 100. The hub device 104 may also be in communication with a clinician (e.g., a hospital), that may be associated with any type of device, 116 to provide information about the stimulation therapy and the user's physiological state to the clinician 116.

Preferably, the sensor(s) 102 and stimulator 110 are 'plug and play' devices with the hub device 104, such that they may be interchanged at-will by the user 100 or clinician 116 in order to build a stimulation system customized to the user's needs/desired therapy. The hub device 104 can interact with the sensors 102 and stimulator 110 via the I/O interfaces 108, which can include existing connectors and protocols such as those based on serial and parallel transmission, USB, BLUETOOTH, near field communication, WiFi, cellular communication, the Internet, and the like. In this manner, the hub device 104 serves as an interface and gateway between the sensors 102 and the stimulator 110 so that 'off the shelf' components not originally configured to cooperate with each other can be integrated in an operational closed-loop stimulation system with ease and little effort or technical configuration from the user 100 or clinician 116.

In more detail with respect to FIG. 1, a user 100 of the system of the present disclosure may wear any number of various smart devices (e.g., a smart watch configured to determine ECG data) having physiological sensors 102 therein. The sensors 102 may provide respiratory information, cardiac information (e.g., from an electrocardiogram/ECG and/or pressure/photoplethysmography sensors), neurological information (e.g., from an electroencephalogram/EEGs), muscle activity information (e.g., from an electromyogram/EMG), and the like. These sensors 102 may collect physiological data before, during, and/or after stimulation. The sensor data is transmitted in real time to the hub device 104 via the I/O interface 108 between the sensor 102 and the hub device 104. As noted above, the transmission may be wired (e.g., over existing connectors and protocols such as USB) or wireless (e.g., via BLUETOOTH, over the Internet, over a local network via WiFi, or the like). Because the hub device 104 serves as an interface, the devices/sensors 102 do not need to be previously configured to work with stimulators or be capable of performing analysis to determine appropriate stimulation.

The processor 106 and/or machine learning system 118 can then process the data to extract stimulation biomarkers (such as modulations on heart rate, ECG waveforms, blood pressure, cytokines and levels thereof, cortisol levels, pupil dilation, eye movements, tremors, gastrointestinal upsets, and the like), and/or operate as a machine learning system that receives the physiological data as an input and outputs a stimulation determination (e.g., whether to begin, stop, or adjust stimulation). When processed at least partly remotely, the hub device 104 may transmit the collected sensor data to a remote machine learning system and/or database 118 for the above-noted analysis and/or storage. In these embodiments, the processor 106 may preprocess the data (e.g., noise filtering) prior to transmission to the machine learning system and/or database 118. In other words, a machine learning system 118 may make the stimulation determination remotely from the hub device 104, and communicate that decision back to the hub device 104. In this manner, the machine learning system 118 may be centrally trained and updated based on collection of sensor data from a plurality of users. Further, the machine learning system 118 is removed from the end user, thereby reducing the complexity and cost of the user devices, such as the hub device 104. Of course in other embodiments any or all of the processing may be performed locally by processor 106.

Without limitation, the storage may comprise a cloud or cloud-based storage using cloud computing. For example, cloud computing may comprise an Internet connection between one or more systems that are operating in the cloud. The cloud may comprise a plurality of systems such that one or more shared resources, such as processing circuits, peripherals, software, data, servers, and the like are provided to any system of the cloud so as to allow access and distribution of services and/or data between the systems of the cloud. In some examples, rather than transmitting the sensor data to the cloud for processing, local processing may instead be used by the hub device 104. The hub device 104 may also itself implement a trained machine learning system such as that described with respect to system 118. In yet other examples, the cloud, local processing, and/or any combination thereof may be used by the hub device 104.

In addition to using the data from sensor(s) 102 for immediate analysis to trigger or adjust stimulation, longitudinal biomarker data collected from sensors 102 may be stored in memory of the hub device 104 or at a remote database 118. Such stored data can then be analyzed to inform future studies of optimal stimulation parameters for maximizing therapeutic benefit. With stored sensor data from a plurality of users, in some embodiments the machine learning systems 118 and/or processor 106 can be trained to identify and detect more robust biomarkers. For example, the machine learning systems 118 can extract features of the sensor data that are indicative of certain disorders within a given population. This information can then be used to better determine when stimulation should be applied by, for example, retraining the machine learning systems 118 with the collected and stored data. Such machine learning systems 118 may also be trained to predict therapeutic outcomes of stimulation given to a particular user, their physiological state determined from the sensor data, and/or given stimulation parameters. In other words, stimulation protocols may be updated based on detected physiological signals. For example, if a given stimulation protocol is insufficient to achieve a desired effect to a biomarker, the stimulation protocol may be adjusted (e.g., increasing amplitude or duration) until the effect is achieved. This adjustment may be to the output of a machine learning system, or as part of retraining of the machine learning system based on the detected physiological signals. In some embodiments, the machine learning systems 118 may also be trained to predict the onset of certain physiological conditions based on the sensor data. In these cases, stimulation may be applied to prevent the onset of the condition Any of the above analyses by machine learning systems 118 and/or the processor 106 may be based on any one or combination of user population data (e.g., age, gender, medical condition, and the like), corresponding stimulation parameters (e.g., collected during or after stimulation), and biomarkers extracted from the sensor data (e.g., ECG data, blood pressure modulations, tremors, gastrointestinal upsets, cytokines and levels thereof, cortisol levels, pupil dilation, eye movements, and/or the like biomarkers that could indicate whether a particular user will benefit from a particular therapy. For example, the analyses may associate or identify specific biomarkers (and levels) with a given medical condition for a given population, and appropriate stimulation protocols. In some particular examples, the trained machine learning system 118 may be configured to extract one or more features of the physiological signal of the user that are indicative of one or more disorder, to predict an outcome based on a stimulation protocol for a given population and/or medical condition associated with particular biomarkers, and to determine when to deliver the electrical stimulation to the user in accordance with a stimulation protocol.

The hub device 104 then operates to control stimulation via the stimulator 110 based on the analysis result of the processor 106 or machine learning systems 118 by outputting a control signal to the stimulator 110. The output signal may identify when to deliver the stimulation, and may include (or be encoded with) the stimulation parameters. Like the sensors 102 and hub device 104, the stimulator 110 may also be a wearable device configured to non-invasively stimulate the user via a skin-surface electrode 114. However, in some embodiments, the stimulator may include an implanted electrode 114.

Stimulation may be automated based on the above analyses, or manually selected by the user 100 or clinician 116. For example, the hub device 104 may be programmed to display a plurality of stimulation protocols via the I/O interface 108 after performing the above analyses and identifying the plurality of stimulation protocols for treatment. The hub device 104 may then be further programmed to receive a selection for one of the plurality of stimulation protocols, and deliver electrical stimulation according to the selected stimulation protocol to treat the one or more disorders.

As with the sensors 102, the stimulator 110 may be of any type that can deliver electrical stimulation to the user 100 based on a control signal. Again, because the hub device 104 serves as an interface, the stimulator 110 need not include any sensors itself or be configured to process any sensor data itself. Further, different stimulators including different electrodes 114 may be used with the hub device 104. For example, in one configuration the hub device 104 may be configured to control delivery of VNS transcutaneously through a skin-surface electrode 114, but in another configuration be configured to control delivery VNS via an invasively placed electrode 114. The hub device 104 is thus configured to control delivery of VNS and the appropriate stimulation parameters according to different anatomic placements of electrodes 114 (e.g., to different locations of the Vagus nerve). In still other embodiments, the hub device 104 may be configured to control delivery of stimulation other than VNS.

Still further, the analysis performed by the processor 106 (and other operations of the processor 106) and/or the machine learning system 118 may also be 'plug and play.' In other words, the analysis of sensor data may depend on which sensors 102 are connected to the hub device 104. Such analysis may be modular, whereby the processor 106 and/or machine learning system 118 is configured to analyze data from each of a plurality of known sensor types. Then, depending on the sensors 102 connected to the hub device 104, the processor 106 and/or machine learning system 118 may selectively utilize different processing modules corresponding to those sensors. Similarly, the modules may be selected based on a desired biomarker.

For example, one processing module may be configured to determine a pre-ejection period (PEP) (latency between electrical depolarization of the ventricles and opening of aortic valve) based on an input from two different connected sensors 102, such as a pressure sensor and an ECG sensor. Therefore, when a determination of PEP is desired for controlling stimulation, the user 100, the hub device 104, and/or the machine learning system 118 may select the 'PEP module' to process sensor data from connected sensors 102. In other embodiments, the processing architecture may be custom designed for a desired set of sensors 102 and type of stimulation. These processing modules and architectures may themselves be machine learning processes, or based on outputs of trained machine learning systems 118 designed to identify biomarkers for desired stimulation therapies.

The processing may also be based on the stimulator 110 connected to the hub device 104. For example, different stimulation parameters may be needed depending on the type of electrode 114 (whether invasive or non-invasive), the power supply abilities of the stimulator 110, and the like. The processor 106 and/or the machine learning system 118 may thus be configured to determine different stimulation parameters depending on whether the stimulator 110 utilizes a skin-surface electrode 114 or an implanted electrode 114.

Any of the above described processing may also employ techniques for improving data sets (e.g., from the physiological sensors) that may be limited, for example, when training the above-described machine learning systems 118. Such techniques may include domain adaptation to enable rapid calibration and improved performance across subjects, and for improving performance within subjects but when sensor 102 alignment is variable. In other words, domain adaptation allows algorithms to adapt to new users or sensor 102 placements by "aligning" each recording to a reference dataset, and then making predictions on the aligned data. This allows algorithms to be robust to new users, and changes in sensor 102 placements for wearable devices. Additionally, data augmentation may be used to manipulate training data to increase the generalization to newer data sets. Such data augmentation may include mixup, cutmix, image transforms, and like functions.

In addition or alternatively, training may be self-supervised to allow the machine learning system 118 to learn the underlying representations of data sets, and then initialize training for a specific data set. Similarly, transfer learning, which is like self-supervised learning but where the system is trained on a large collection of data and then fine-tuned on a newer subject, may be utilized.

Still further, manifold analyses may be utilized. Such analyses can involve reducing the dimensionality of some aspect of the data (e.g., high dimensional versions of inputs to the machine learning system 118 or system activation functions). These analyses and dimensionality reductions can help visualize the machine learning system's 118 state.

As suggested above, the above-described architecture allows the stimulation system described herein to operate as a 'plug and play' platform. In other words, the hub device 104 can interact with different sensors 102 and types, and from different manufacturers (e.g., 'off the shelf' monitoring devices). The particular sensors 102 and stimulator 110 may be selected by the user 100 or clinician 116 based on a desired use of the system (e.g., the particular disorder being treated, or the particular therapy being delivered).

At any point (before, during, or after stimulation and/or collection physiological data from the user 100), the raw or any processed data from the sensors 102, the analysis result from the processor 106 and/or machine learning system 118, and/or alerts may be output to the user 100. The output may be via, for example, a display screen, speaker, printer, or like output device of the hub device 104. The alerts may be output when the hub device 104 identifies a physiological abnormality or error (e.g., with data collection or reduced stimulation efficacy due to central desensitization). As previously mentioned, the output may additionally or alternatively include a display of stimulation protocols, for example, based on an analysis of features extracted from the sensor data or associated with a desired treatment. The data, analysis results, and/or alerts may also be transmitted to a clinician 116 for remote monitoring. Transmission to the clinician may also occur wirelessly over the Internet, cellular communication network, or the like.

In some embodiments the hub device 104 or I/O interface 108 thereof may be a smart phone, tablet, or like personal device. In these cases, and when the hub device 104 is a separate device, the hub device 104 and processor 106 may be configured to operate using ANDROID, iOS, or like operating systems and platforms to simplify the end user requirements and complexity of hub device 104. Nevertheless, embodiments in which analysis or machine learning operations are preformed can be based on custom computing architectures embodied on computing systems remote from the hub device 104. Such remote computing systems may be in communication with the hub device 104, and receive data from and transmit data to the hub device 104 via wired or wireless communication, including the Internet and cellular communication networks. Of course, other suitable processing platforms may be utilized to implement the present disclosure.

Figure 2:
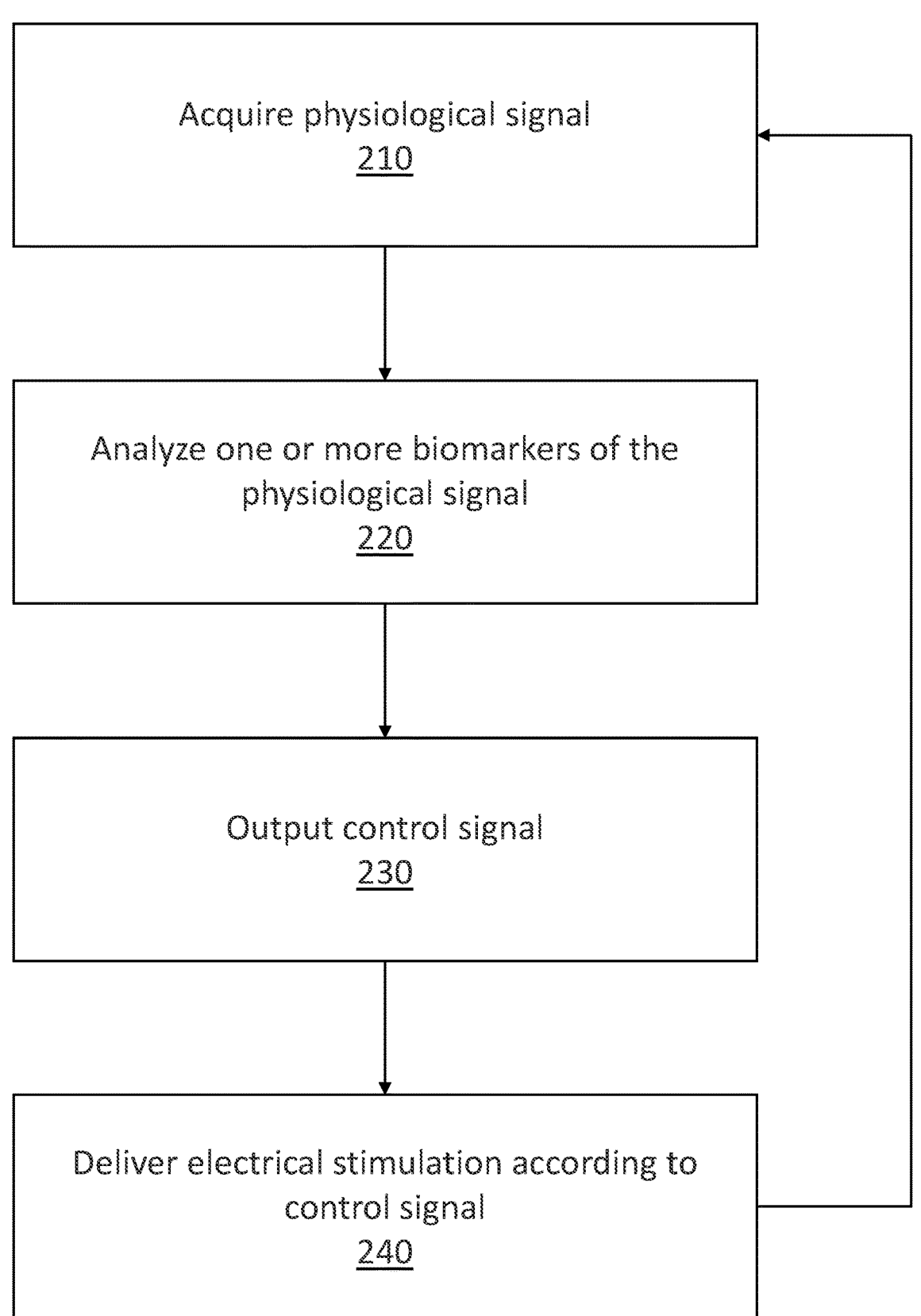
FIG. 2 illustrates an example controlled stimulation method according to the present disclosure.

FIG. 2 illustrates an example method for using the system of FIG. 1 (or as otherwise described herein) for closed-loop stimulation control. Initially at block 210, the method includes acquiring a physiological signal of a user, for example, with sensor(s) 102. At block 220, the method includes analyzing one or more biomarkers that are indicative of one or more disorders and/or stimulation timings. The biomarkers may be extracted from the acquired physiological signal and analyzed by the processor 106 of the hub device 104 and/or the machine learning systems 118. At block 230, the method includes outputting a stimulation control signal based on the analyzed biomarker to the stimulator 110. Then at block 240, the method includes delivering electrical stimulation to the user 100 via the stimulator 110 based on the control signal. The method then repeats itself. In this manner, the output of the stimulator 110 is automatically controlled by the hub device 104 based on analyzed biomarkers associated with a disorder being treated by the stimulation and extracted from physiological signals acquired by the sensor(s) 102.

As suggested above, closed-loop stimulation according to the present disclosure may be applied to treat many different disorders. For example, such disorders may relate to cardiovascular disorders, stress disorders, and addictions.

In one example related to cardiovascular disorders, the above analyses of physiological signals relies on the pre-ejection period (PEP) (as discussed above) as a more robust biomarker than conventional vital signs, such as heart rate and blood pressure, which fail to robustly measure stimulation efficacy. Further, the PEP can be used to optimize VNS parameters, and to dynamically adjust stimulation parameters during stimulation to achieve maximal therapeutic benefit. Because PEP is based on both the electrical depolarization and the physical opening of the aortic valve, the PEP may be determined by analysis of both an electrocardiogram (ECG) and continuous non-invasive blood pressure (CNIBP) or like pulse wave measurement (e.g., photoplethysmography (PPG)). Accordingly, ECG, CNIBP, PPG, and like sensors may be utilized individually or in any combination as sensors 102 that provide data to hub device 104. This data can be used to provide continuous biomarker feedback during stimulation over the course of a therapy.

In another cardiovascular example, the hub device 104 may be used to implement closed-loop VNS for the detection and treatment of myocardial ischemia events, as described in U.S. application Ser. No. 17/207,081 filed on Mar. 19, 2021 and U.S. Pat. No. 10,953,229, issued on Mar. 23, 2021, each being entitled "THERAPEUTIC WINDOW FOR TREATMENT OF ISCHEMIA BY VAGUS NERVE STIMULATION" and incorporated by reference herein in their entireties.

Regarding stress disorders, the sensors 102 may continuously monitor physiological stress metrics (e.g., heart rate, blood pressure, etc.) and reactively cause the stimulator 110 to deliver a stimulation (e.g., VNS). Utilizing the hub device 104 allows users to receive automated VNS delivery during exposure therapy, without requiring interaction with a clinician. Accordingly, the therapy may also be delivered throughout the day if/when the user experiences a stress episode (e.g., a truck backfiring that triggers a PTSD episode). Thus, therapy is not limited only to when stresses are triggered in a clinical setting, and is not subject to costs and time commitments of traditional clinical exposure therapy. Further, the determination of when to deliver stimulation is not subject to human error. And where the clinician remains involved in the therapy, the clinician may devote more resources to administering the exposure therapy.

As already discussed, a user 100 undergoing a stress therapy may wear one or more non-invasive physiological monitoring devices having sensors 102 for collecting physiological data. These monitoring devices may be connected to a hub (such as the user's smartphone), where the data is analyzed to detect stress events experienced by a user 100. The stress events may be detected as pre-defined patterns of physiological responses (e.g., elevated heart rate in the absence of strenuous activity, or the like). These pre-defined patters may be identified by a trained machine learning system 118 implemented by the hub device 104, or the hub device 104 may be configured to detect stress events by itself implementing a trained machine learning system 118 (e.g., receiving the physiological data from the wearable devices as an input, and outputting a determination of a stress event). Upon detection of the stress event, the hub device 104 may control the stimulator 110 to begin stimulation. As noted, VNS during the stress event can enhance fear extinction and provide the user with anxiety relief. This relief may also be identified by the hub device 104 by recognizing a return of the physiological responses to normal or baseline levels.

Treatments similar to those for stress disorders may be used for other anxiety-related neurological disorders, such as PTSD, phobias, obsessive-compulsive disorder (OCD), addiction, and the like. In these instances, the biomarkers can include cytokines and levels thereof, cortisol levels, heart rate, pupil dilation, eye movements, tremor, gastrointestinal upsets, and the like. Accordingly, sensors 102 may include those capable of detecting such features, including ECG sensors, pressure/photoplethysmography sensors, electromyography/EMG sensors, electroencephalography/EEG sensors, chemical reagents and like sensors for detecting biochemical levels in sweat or other fluids, eye trackers, and the like.

In view of the above, and as also suggested, the system herein can be customized to each user. For example, a hospital system, a research lab, and a warfighter could all implement different embodiments of the system as different combinations of sensors 102, processor 106 and/or machine learning system 118 analyses, and stimulators 110. In other words, the system described herein can be adapted to any use by selecting appropriate sensors 102, processors 106 and/or machine learning systems 118 and analyses, and stimulators 110. These elements may be individually designed for other and distinct purposes (e.g., heart rate monitoring during exercise) but, when implemented with the hub device 104, forms a customized stimulation system. Still further, the use of proven 'off the shelf' monitoring devices for sensors 102, and stimulators 110 can lend confidence to clinicians using the hub device 104 because they can trust those existing devices.

Figure 3:
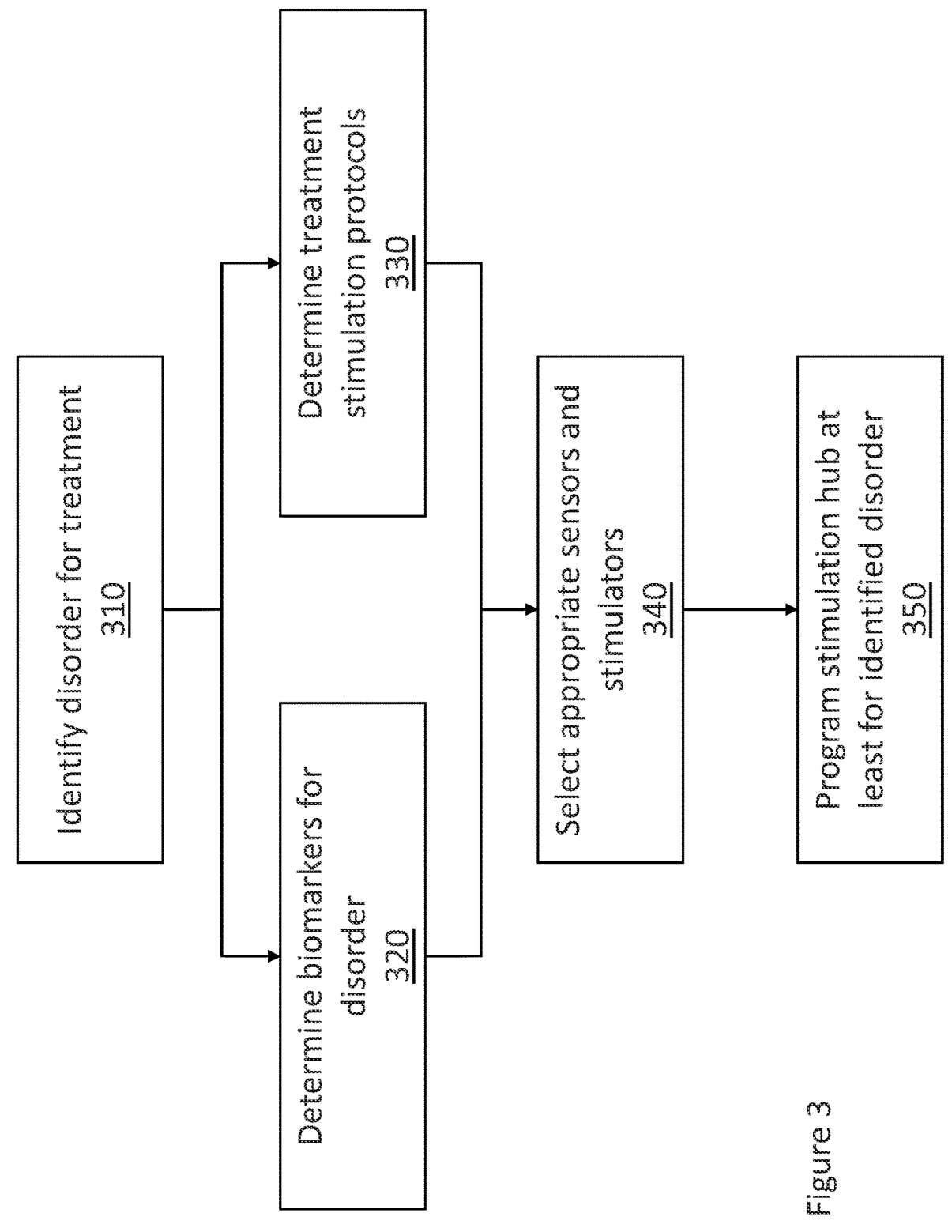
FIG. 3 illustrates an example design and customization method for a stimulation hub system according to the present disclosure.

An example of such design and customization is illustrated with respect to FIG. 3. As shown therein, at block 310 a disorder to be treated by the system is first identified. Then at blocks 320 and 330, the appropriate biomarkers and stimulation protocols associated with that disorder are determined. With the particular biomarkers and stimulation protocols known, the corresponding sensors and stimulators can be selected at box 340. For example, for the treatment of cardiovascular disorders in which PEP is a desired biomarker, the selected sensors may be ECG and blood pressure or pulse wave measurement sensors. Finally, at box 350, the hub device 104 may be programmed to appropriately communicate with the selected sensors and stimulators, and to associate the determined biomarkers and stimulation protocols. For example, the hub device 104 may be programed to perform analysis of the physiological signals from the sensors to identify threshold levels of the biomarkers that should result in a given stimulation protocol. In other words, the hub device 104 may be programmed to identify that when a user's PEP time exceeds or falls below a predetermined threshold (e.g., as programmed in the processor of the hub device 104), indicating a potential arrhythmia or like cardiac event trigger, the stimulator should be controlled to execute a corresponding stimulation protocol to treat the cardiac event.

Depending on the embodiment, the hub device 104 may be programmed to perform the appropriate analyses for more the treatment of more than one disorder. In this manner, the hub device 104 may be easily adapted to treat other disorders without requiring significant (if any) changes to the hub. Rather, the only modifications to the system for treating the new disorder may be in the selection and use of new sensors and/or stimulators while retaining the original hub device 104. In some embodiments, updates (such as new analysis processes) may be remotely pushed to the hub device 104. For example, such updates (or original programming) may include simply adding the above-noted 'PEP module' to the hub device 104. Again, this means that the hub device 104 may be easily updated or used to treat any disorder with minimal changes to the system.

While various features are presented above, it should be understood that the features may be used singly or in any combination thereof. Further, it should be understood that variations and modifications may occur to those skilled in the art to which the claimed examples pertain.

What is claimed is:

1. A stimulation system comprising:
a sensor configured to detect a physiological signal of a user, the physiological signal having a biomarker therein associated with a disorder of the user;
a stimulator configured to deliver electrical stimulation to the user; and
a hub device configured to receive the physiological signal from the sensor and to output a control signal to the stimulator,
wherein the control signal causes the stimulator to deliver the electrical stimulation to the user according to a stimulation protocol, the stimulation protocol treating the disorder,
wherein the hub device is configured to output the control signal based on the biomarker of the received physiological signal, and
wherein the hub device is configured to generate, without being reprogrammed, another control signal for treating another disorder based on a biomarker not included in the physiological signal received from the sensor.

2. The stimulation system of claim 1, further comprising a database configured to store detected physiological signals and/or associated stimulation protocols from a plurality of users, the physiological signals being transmitted to the database by a hub device associated with each of the plurality of users.

3. The stimulation system of claim 1, wherein the disorder is a cardiovascular disorder and the biomarker is a pre-ejection period.

4. The stimulation system of claim 1, wherein the hub device is in communication with another device associated with a clinician and is configured to transmit information indicating a physiological state of the user and/or the delivery of electrical stimulation to the another device associated with the clinician.

5. The stimulation system of claim 1, wherein the electrical stimulation is delivered to the Vagus nerve of the user.

6. The stimulation system of claim 1, wherein the sensor and/or the stimulator are external to and distinct from the hub device, and the hub device is portable.

7. The stimulation system of claim 1, wherein the hub device is configured to change the control signal to the stimulator based on the physiological signal received from the sensor.

8. A stimulation system comprising:
a sensor configured to detect a physiological signal of a user, the physiological signal having a biomarker therein associated with a disorder of the user;
a stimulator configured to deliver electrical stimulation to the user; and
a hub device configured to receive the physiological signal from the sensor and to output a control signal to the stimulator,
wherein the control signal causes the stimulator to deliver the electrical stimulation to the user according to a stimulation protocol, the stimulation protocol treating the disorder,
wherein the hub device is configured to output the control signal based on the biomarker of the received physiological signal,
wherein the sensor and/or the stimulator are external to and distinct from the hub device, the hub device is portable, and
wherein the hub device is programmed to deliver electric stimulation to the user according to a plurality of stimulation protocols for treating a plurality of disorders without being reprogrammed.

9. The stimulation system of claim 8, further comprising:
a trained machine learning system remote from, and in communication with, the hub device,
wherein the trained machine learning system is configured to:
determine whether to deliver the electrical stimulation, and/or to determine the stimulation protocol, based on the physiological signal; and
transmit the determination to the hub device,
wherein the hub device is further configured to transmit the physiological signal of the user to the trained machine learning system, and
wherein the control signal is based on the determination transmitted by the trained machine learning system.

10. The stimulation system of claim 9, further comprising:
a remote database configured to store detected physiological signals and/or associated stimulation protocols from a plurality of users, the physiological signals being transmitted to the remote database by a hub device associated with each of the plurality of users,
wherein the trained machine learning system is repeatedly retrained based on the detected physiological signals and/or associated stimulation protocols stored in the remote database.

11. The stimulation system of claim 10, wherein the trained machine learning system is configured to:
extract one or more biomarkers of the physiological signal of the user that are indicative of one or more disorders;

13

14 predict an outcome of the stimulation protocol based on an analysis of the one or more biomarkers; and determine, based on the prediction, whether to deliver the electrical stimulation the user according to the stimulation protocol.

12. The stimulation system of claim 8, wherein the hub device is in communication with another device associated with a clinician and is configured to transmit information indicating a physiological state of the user and/or the delivery of electrical stimulation to the another device associated with the clinician.

13. The stimulation system of claim 8, wherein the electrical stimulation is delivered to the Vagus nerve of the user.

14. A stimulation method comprising:

identifying a disorder for treatment;

determining a biomarker indicative of the disorder;

determining a treatment stimulation protocol;

selecting a sensor configured to detect the biomarker;

selecting a stimulator configured to apply the treatment stimulation protocol; and configuring a hub device external to and distinct from the sensor and the stimulator to apply the treatment stimulation protocol based on the biomarker detected by the sensor, the sensor and the stimulator being connected to the hub device; then:

identifying a second disorder for treatment;

determining a second biomarker indicative of the second disorder;

determining a second treatment stimulation protocol;

selecting a second sensor configured to detect the second biomarker;

selecting a second stimulator configured to apply the second treatment stimulation protocol; and reconfiguring the hub device to apply the second treatment stimulation protocol based on the second biomarker detected by the second sensor.

15. The stimulation method of claim 14, wherein the disorder is a cardiovascular disorder and the biomarker is a pre-ejection period.

16. The stimulation method of claim 14, wherein the hub device is in communication with another device associated with a clinician and is configured to transmit information indicating a physiological state of the user and/or the delivery of electrical stimulation to the another device associated with the clinician.

17. The stimulation method of claim 14, wherein the electrical stimulation is delivered to the Vagus nerve of the user.

18. The stimulation method of claim 14, wherein the hub device is portable.

19. The stimulation method of claim 14, wherein the hub device is configured to change a control signal to the stimulator based on the physiological signal received from the sensor.

* * * * *